(12) United States Patent
Duong et al.

(10) Patent No.: US 9,468,484 B2
(45) Date of Patent: Oct. 18, 2016

(54) AUTOMATED BALLOON CATHETER FLUID PURGING SYSTEM

(71) Applicants: Thach Buu Duong, Tustin, CA (US); Min Frank Zeng, Irvine, CA (US)

(72) Inventors: Thach Buu Duong, Tustin, CA (US); Min Frank Zeng, Irvine, CA (US)

(73) Assignee: Cryofocus Medtech (Shanghai) Co. Ltd., Shanghai (CN)

( * ) Notice: Subject to any disclaimer, the term of this patent is extended or adjusted under 35 U.S.C. 154(b) by 434 days.

(21) Appl. No.: 14/026,010

(22) Filed: Sep. 13, 2013

(65) Prior Publication Data

US 2015/0080794 A1  Mar. 19, 2015

(51) Int. Cl.
| | | |
|---|---|---|
| *A61B 18/02* | (2006.01) | |
| *A61M 25/10* | (2013.01) | |
| *A61M 1/10* | (2006.01) | |
| *A61B 18/00* | (2006.01) | |

(52) U.S. Cl.
CPC ............... *A61B 18/02* (2013.01); *A61M 1/10* (2013.01); *A61M 25/10186* (2013.11); *A61B 2018/0022* (2013.01); *A61B 2018/0212* (2013.01); *A61B 2018/0262* (2013.01); *Y10T 137/7761* (2015.04)

(58) Field of Classification Search
CPC .......... A61B 18/02; A61B 2018/0022; A61B 2018/0212; A61B 2018/0262; A61M 25/10186; A61M 1/10; Y10T 137/7761
See application file for complete search history.

(56) References Cited

U.S. PATENT DOCUMENTS

2011/0071465 A1\* 3/2011 Wang ...................... A61M 1/28
  604/67
2015/0283361 A1\* 10/2015 Jin ................... A61M 25/10186
  604/500

FOREIGN PATENT DOCUMENTS

WO  WO 2013109293 A1 \* 7/2013 ...... A61M 25/10186

\* cited by examiner

*Primary Examiner* — Emily Schmidt
*Assistant Examiner* — Lauren M Peng
(74) *Attorney, Agent, or Firm* — Raymond Sun

(57) ABSTRACT

A fluid purging system has a spring-energized relief valve having an inlet port that is coupled to a fluid chamber to receive incoming fluid, and an outlet port through which incoming fluid is relieved. The outlet port is fluidly coupled to a pressurized chamber. The fluid purging system also includes an electro-mechanical pressure switch, and an electrically operated solenoid valve which functions as a pressure exhaust valve. The pressure switch and the solenoid valve are in fluid communication with the pressurized chamber.

15 Claims, 4 Drawing Sheets

AUTOMATED BALLOON CATHETER FLUID PURGING SYSTEM

BACKGROUND OF THE INVENTION

1. Field of the Invention

The present invention relates to catheter systems, and in particular, to an automated balloon catheter fluid purging system.

2. Description of the Related Art

A typical industrial fluid purging system normally uses a pressure sensor (i.e. pressure switch, pressure transducer, etc.) to detect the fluid pressure within the pressurized chamber, and relieves high pressure directly from the pressurized chamber through an exhaust valve. This typical industrial fluid purging system does not incorporate a relief valve ahead of the pressure sensor, thereby making it simpler to implement. However, this arrangement is not practical for medical device applications. Specifically, the placements of these two components are critical. If the two components (pressure sensor and exhaust valve) are mounted within a system enclosure, a long fluid connection line is necessary. This will result in greater volume added to the balloon chamber, making it more difficult to evacuate it of trapped air. It is critical to remove all air pockets from a balloon chamber prior to inflation, Otherwise, air will be introduced into the vessel if the balloon bursts. Having a larger volume will make the air evacuation process more time-consuming and difficult. In addition, a larger volume requires more fluid to fill. As a result, this setup is less efficient and increases overall procedure time.

Mounting the pressure switch and the exhaust solenoid valve directly to the catheter would solve the above issues, but would make the assembly very cumbersome to handle. This arrangement exposes dangling electrical components with their electrical wirings running from the catheter to the system. This setup is also expensive since the two components are disposable.

Regardless of the setups described above, a typical industrial purging system is not sensitive and quick to detect pressure spikes within the system because the detection/switching pressure of the pressure sensor has to be set at a value above the working pressure or balloon pressurization pressure. This is a result of two dynamics. First, pressurization of the balloon chamber is normally performed manually, resulting in variations in the pressure generated. The variations/fluctuations in pressure generated due to either user error or the equipment needs to be considered when determining the working pressure (i.e., balloon pressurization pressure). Second, the pressure sensor has a wide tolerance range at a set point. The lower value of the set point has to be used when determining the working pressure. Otherwise, the system might trigger a false alarm. When these two dynamics are considered together, the working pressure has to be below the low end of the pressure sensor's tolerance range minus the variations cause by the user. With the working pressure set at a value below the pressure sensor's trigger pressure, leaked gas needs additional time to accumulate enough volume within the balloon chamber to create a pressure rise reaching the detection/switching pressure of the pressure sensor. This will delay the response time, making the system less responsive in detecting gas leakage. However, reducing system response time is very critical in maximizing system performance.

There is currently no known in the market today for an automated balloon catheter fluid purging system, but there is a need, especially for catheters that have potential to release gas or foreign fluids into the human body/arterial vessel. Catheters that carry gas through a delivery system placed inside the human body can potentially break and leak gas. A balloon assembly covering the potential leakage section of the catheter can be used to capture leaked gas. However, balloon catheters of this type need a safety purging system to relieve buildup pressure preventing potential trauma. A balloon catheter is normally pressurized using saline to a predetermined working pressure. When foreign fluid leaks into the balloon chamber, its internal pressure raises.

An automated computer controlled purging system is needed because a manual monitoring and purging system does not provide the reliability, consistency, and instantaneous response needed to safeguard against abnormal pressure rises, and especially when there is a gas leakage from the gas delivery line. Pressurized gas can rapidly fill up a small confined balloon volume and cause significant pressure rise in short period of time. High pressure or over-pressurization can be detrimental to the patient:

a. Internal pressure adds stress on the component and causes it to expand. Over-pressuring the balloon, for example, can inflate the balloon to be larger than originally intended. This could stretch the patient's arterial wall beyond elastic limit and cause permanent damage.

b. High internal pressure will stress the material to its rupture point where it will burst open and release its fluid.

c. Unwanted fluid (such as pressurized gas, cryogen, etc.) can be released into the patient and cause trauma and even death.

d. A bursting balloon can cause physical damage to its surrounding (i.e., arterial wall) as the high pressure ruptures the balloon wall, pressing the torn material outward, and further stretching the surrounding wall, creating damages.

It is important to measure pressure instead of measuring flow rate or fluid accumulation level. To begin with, measuring pressure allows for instantaneous detection of leakage across the relief valve. Pressure creates stress within the material that bounds it, and should be controlled below a safe limit. In addition, pressure is easy to detect by using a high sensitivity and cost-effective pressure switch. Finally, detecting pressure is more cost-effective than detecting flow/leakage rate or fluid accumulation level, which requires a bulkier and more expensive flow meter or level indicator.

SUMMARY OF THE INVENTION

To overcome the above-mentioned deficiencies, an object of the present invention is to provide an automated balloon catheter fluid purging system.

To accomplish these objectives, the present invention provides a fluid purging system that has a spring-energized relief valve having an inlet port that is coupled to a fluid chamber to receive incoming fluid, and an outlet port through which incoming fluid is relieved. The outlet port is fluidly coupled to a pressurized chamber. The fluid purging system also includes an electro-mechanical pressure switch, and an electrically operated solenoid valve which functions as a pressure exhaust valve. The pressure switch and the solenoid valve are in fluid communication with the pressurized chamber. The fluid purging system of the present invention can be used with a catheter assembly having a balloon adjacent its distal end, with a fluid chamber defined adjacent the balloon. The relief valve would be fluidly connected to the fluid chamber.

The fluid purging system of the present invention can automatically detect and purge both the gas leakage from the catheter delivery system and the fluid used to pressurize the balloon out of the system. The fluid purging system of the present invention can be used with, among other products and systems, a cryocatheter with a balloon-enclosed distal end, a cryoballoon ablation catheter, and cryoablation probes.

The fluid purging system of the present invention serves as a safety feature to:

a. maintain working pressure within the balloon under a certain level (through the use of a relief valve);

b. detect abnormal pressure spikes/leakage across the relief valve (through the use of a pressure switch);

c. prevent over-pressurization by purging pressurized fluid and relieving compressed fluid (through the use of a solenoid valve as an exhaust valve);

d. communicate to a computer control system to stop further inflow of fluid to the balloon chamber and/or the catheter delivery lines, and to purge inflow fluids from the system.

The present invention overcomes the weakness of a typical industrial purging setup by incorporating a relief valve positioned ahead of the pressure switch and an exhaust valve. Mounting the relief valve directly to the catheter optimizes the balloon chamber volume, resulting in no change in balloon preparation time prior to fluid injection. A single fluid purging tube connecting the exhaust port of the relief valve to the purging connector of the mechanical system is provided. In normal operation mode, this tube is empty of fluid. The purging connector is in fluid communication with the pressure switch and the exhaust solenoid valve that are attached within the system enclosure.

Mounting the relief valve directly to the catheter also provides other advantages. First, the rate of pressure rise due to a constant gas leakage within an optimized or smaller balloon chamber is faster as predicted by the natural gas law. The natural gas law dictates that pressure increases linearly with additional mass gained. For larger balloon chambers, the rate of pressure rise is slower for the same amount of mass added or gas leaked into the balloon chamber. As a result, the present system can detect and respond earlier when encountering an abnormal pressure spike situation. Second, mounting the relief valve directly to the catheter optimizes the gas escape path. Leaked gas from the distal end has to travel to the relief valve to be relieved. Shortening this passage reduces balloon fluid resistance and allows the leaked gas to push its way into the relief valve more quickly. This also benefits the response time of the system.

The present invention allows the system to be more sensitive in detecting gas leakage. This is possible because the present invention is more forgiving of user errors and component tolerance. The present invention allows the user to fill and pressurize the balloon chamber right at, or near, the cracking pressure of the relief valve. Preloading the system pressure in this manner eliminates the issues of pressure tolerance of the relief valve, and user induced errors. A small amount of fluid leaked across the relief valve during the balloon filling process is tolerable because the purging tube has an empty volume that can be used to store liquid without triggering the pressure switch. A gas leakage into the balloon chamber from the catheter delivery system will instantly escape the relief valve and be detected by the pressure sensor.

DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
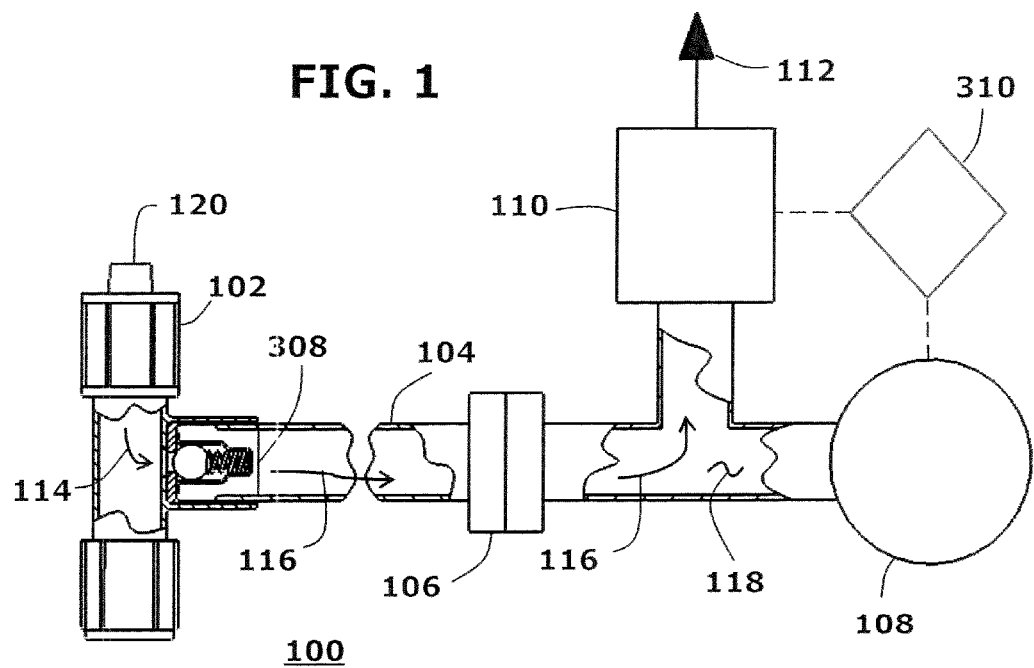
FIG. 1 illustrates a fluid purging system according to the present invention.

Referring to FIG. 1, the present invention provides a fluid purging system 100 that receives incoming fluid 114 through an inlet port 120 of a relief valve 102. The relief valve 102 is a standard spring-energized relief valve having a differential cracking pressure pre-set within the pressure range of 20 to 750 psig. The relief valve 102 acts like a check valve by allowing flow in one direction and restricting flow in the reverse direction. Flow through the relief valve 102 is possible when the internal fluid pressure rises above the cracking pressure of the relief valve 102. For the present invention, the cracking pressure can be set within the range of 30 psig to 550 psig. Normally, the working pressure of incoming fluid 114 is below the cracking pressure. The relief valve 102 receives and contains incoming fluid 114 until an abnormal pressure spike occurs. During this over-pressurization, the relief valve 102 purges excess pressure by relieving incoming fluid 114. The relieved fluid 116 exits the relief valve 102 through a relieving port 308 and into a purging tube 104. The purging tube 104 can be made from a flexible tubing material such as polyurethane, nylon, silicone, or PVC. The purging tube 104 is connected to a purging connector 106 allowing relieved fluid 116 to enter a pressurized chamber 118. The pressurized chamber 118 is in fluid communication with an electro-mechanical pressure switch 108 and an electrically controlled purging solenoid valve 110.

The pressure switch 108 and the purging valve 110 connect to a computer control system 310 which is driven by proprietary computer-controlled software. The pressure switch 108 mechanically detects over-pressurization conditions and electronically communicates to the computer control system. The pressure switch 108 is designed with a switching pressure less than the cracking pressure of relief valve 102. The lower switching pressure allows the system to detect minute amounts of pressure rises and to take appropriate measure to prevent unsafe operating condition. In the present invention, the pressure switch 108 has a switching pressure within the range of 0.10 psig to 25.0 psig. Once the pressurization chamber 118 reaches an internal pressure of 0.10 psig to 25.0 psig or an over-pressurization condition, the pressure switch 108 sends an electrical signal to the computer control system. An activation signal is then transmitted to the purging solenoid valve 110 to open and release purged fluid 112 from the system. The purging solenoid valve 110 remains open until pressure within the pressurized chamber 118 is reduced below the level of the switching pressure. At this point, the control system transmits an electrical signal to deactivate and close the solenoid valve 110.

Figure 2:
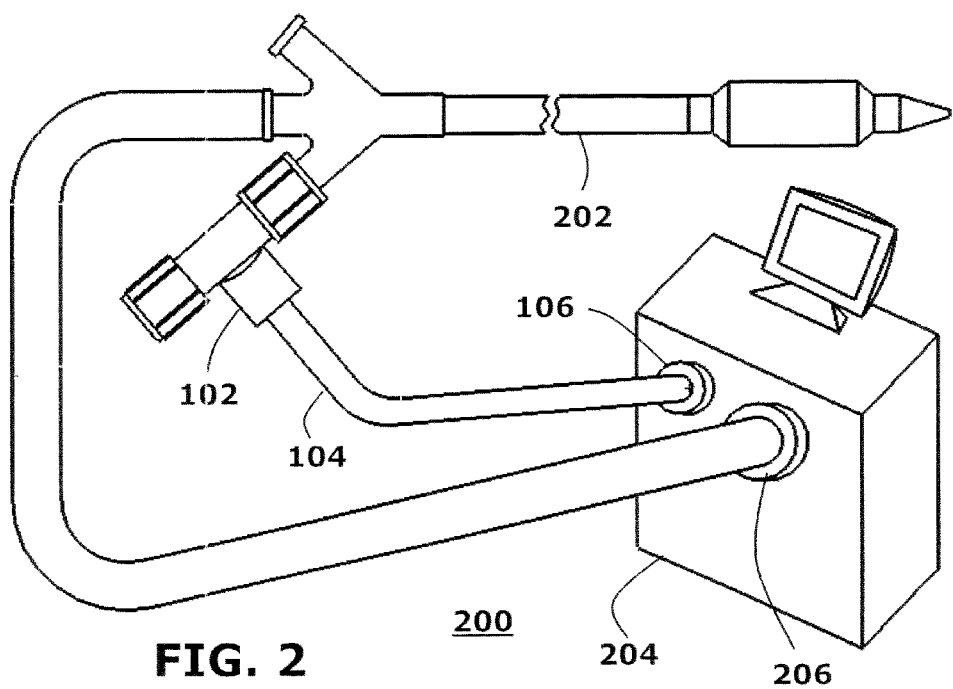
FIG. 2 illustrates a cryoablation system that includes the fluid purging system of FIG. 1.
Figure 3:
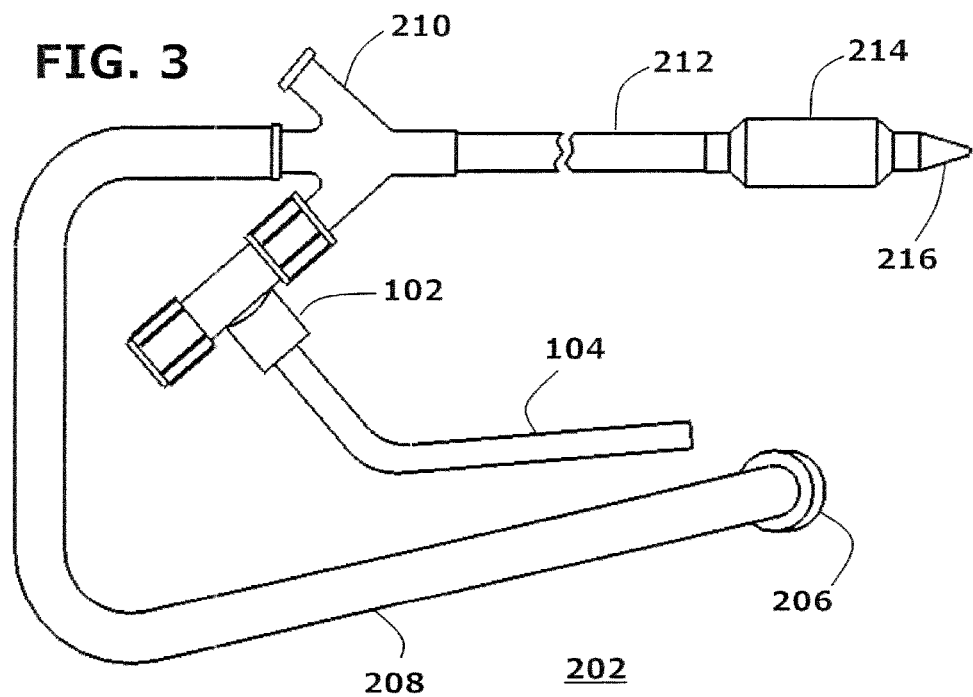
FIG. 3 illustrates a portion of the cryoablation system of FIG. 2.
Figure 4:
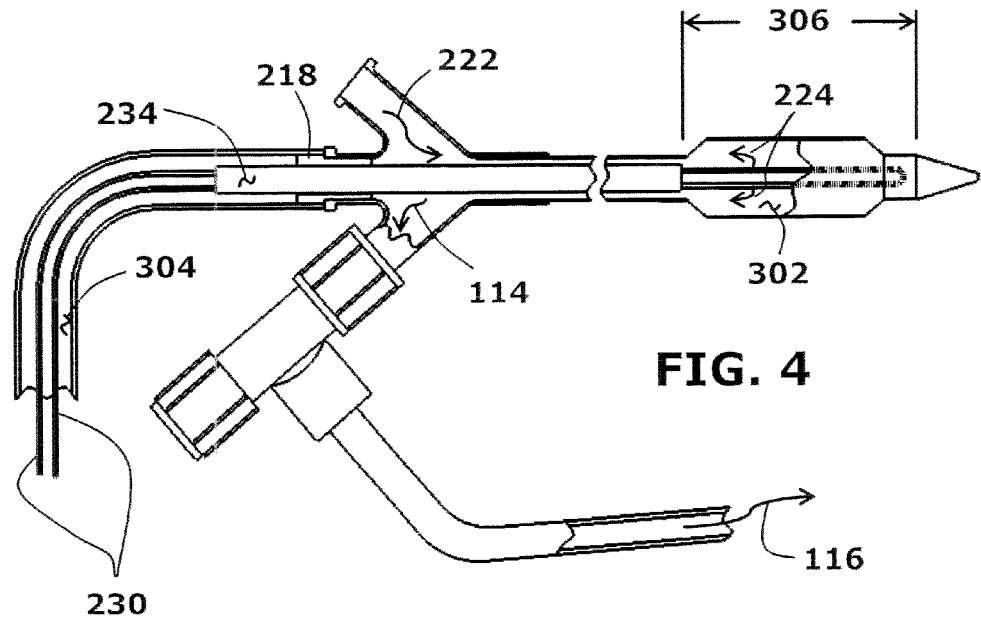
FIG. 4 is a cross-sectional view of portions of the cryoablation system of FIG. 2.
Figure 5:
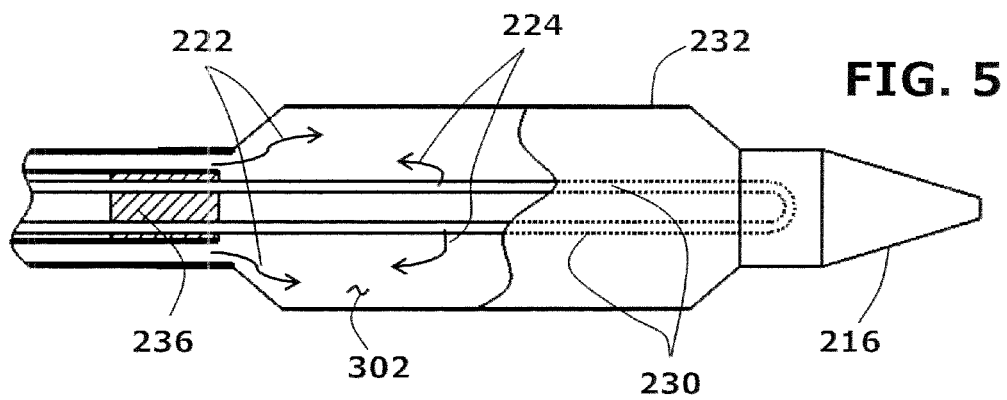
FIG. 5 is an enlarged cross-sectional view of the distal end of the catheter of FIG. 2.
Figure 6:
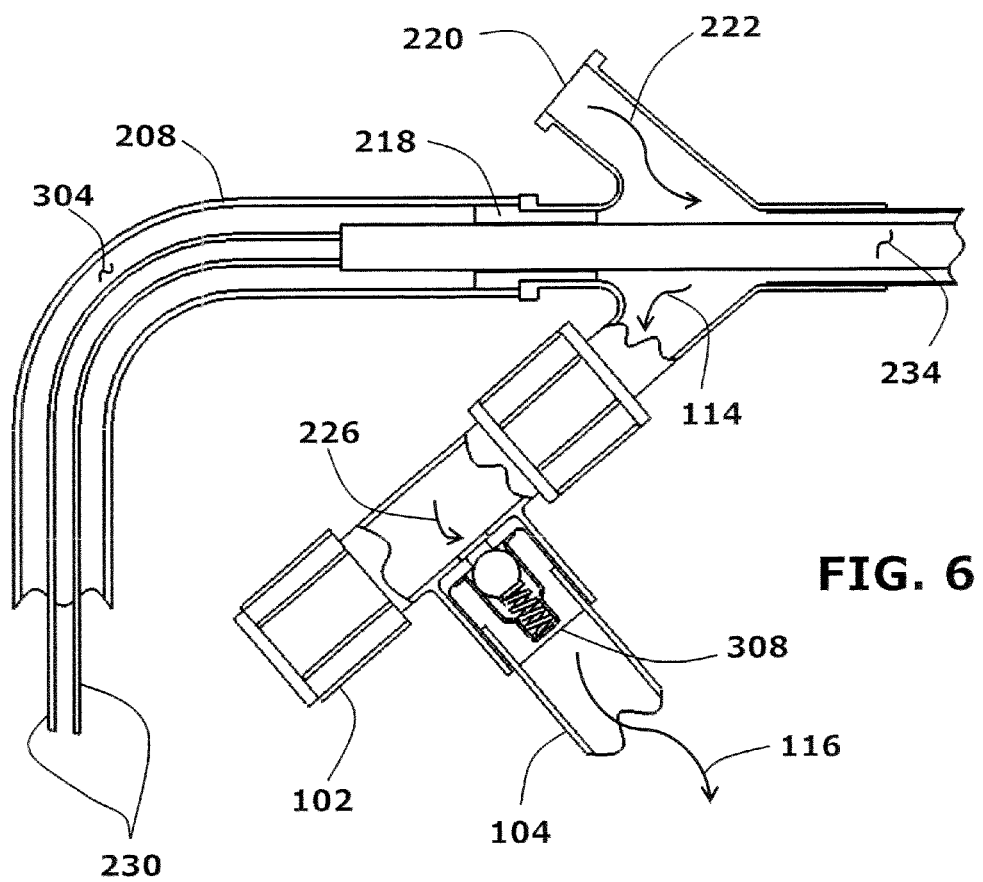
FIG. 6 is a cross-sectional view of portions of the cryoablation system of FIG. 2.
Figure 7:
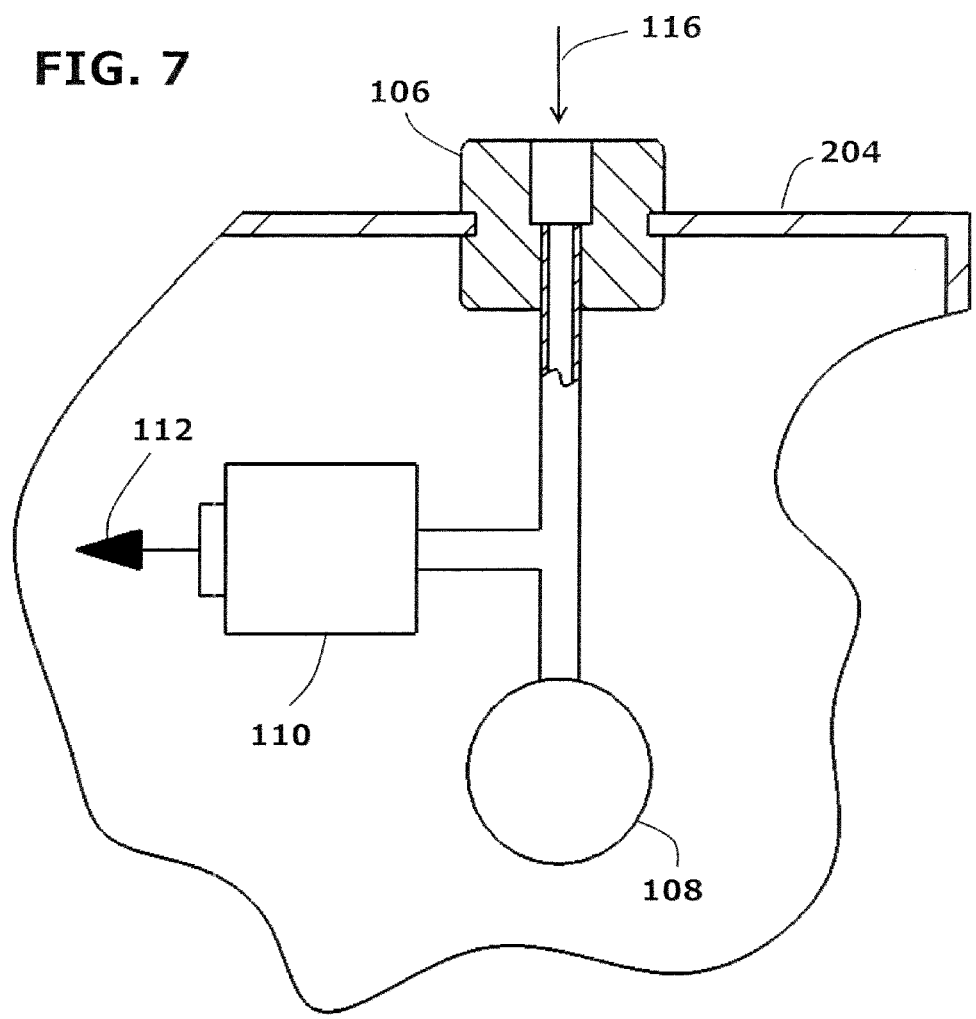
FIG. 7 illustrates the operation of the fluid purging system of FIG. 1.

The fluid purging system 100 described above can be integrated into a cryoablation system 200 as shown in FIG. 2. The cryoablation system 200 includes a balloon catheter 202 that is connects to, and receives working fluid from, an ablation system 204 through a catheter connector 206. The fluid purging system 100 connects to the catheter 202 at one end. The other end of the fluid purging system 100 is installed within the ablation system 204 starting from the purging connector 106 and extending to the pressure switch 108 (which is inside the housing for the ablation system 204). The ablation system 204 contains, at a minimum, mechanical mounting and electrical connections for the pressure switch 108 and the purging solenoid valve 110, as well as the computer control system 310.

Referring now to FIGS. 3-7, catheter 202 contains two delivery lines 230 positioned longitudinally along the center of an outer tube 208. The catheter connector 206 is in fluid communication with the delivery lines 230 and forms an airtight connection with the proximal end of the outer tube 208. The delivery lines 230 are actually comprised of a single line 230 that extends from the catheter connector 206 to the distal end 306 of the catheter 202, and then loops back to the catheter connector 206. The second (distal) end of outer tube 208 forms an airtight seal 218 with the catheter lumen 234 and four-port connector 210. A portion of the delivery line 230 is positioned longitudinally along the center of the catheter lumen 234 extending from near the airtight seal 218 to the distal end 306. An airtight seal 236 formed between the catheter lumen 234 and the delivery tubes 230 at the distal end 306, to form a dry chamber 304. The dry chamber 304 is defined by the volume surrounded by the catheter connector 206, the outer tube 208, the airtight seal 218, the catheter lumen 234, and the airtight seal 236.

A wet chamber 302 forms an outer layer that encloses a portion of the length of the dry chamber 304. The wet chamber 302 is defined by the volume bounded by the airtight seal 218, the four-port connector 210, the balloon tube 212, the balloon 214, and the catheter tip 216. Balloon fluid 222 enters the wet chamber 302 through a port 220 on the four-port connector 210, and pressurizes the balloon 214. The wet chamber 302 receives the balloon fluid 222 and captures any leaked working fluid 224 that escapes from the delivery lines 230. Fluid purging system 100 connects to the four-port connector 210 to receive incoming fluid 114. Incoming fluid 114 can be a combination of the balloon fluid 222 and/or leaked working fluid 224. As the incoming fluid 114 pressure rises above a predetermined safety limit, the system 100 relieves purged pressure 112 from the system 100, relieves pressurized fluids, and shuts down all operations.

The following is one non-limiting way of mechanically integrating the fluid purging system 100 into the ablation system 204. The relief valve 102 connects directly to the wet chamber 302 to receive incoming fluid 114. Positioning the relief valve 102 at this location provides many advantages. First, the volume of fluid that is required to fill up the wet chamber 302 to pressurize balloon 214 is minimized. As a result, less time and effort is required to evacuate and fill the wet chamber 302. Second, positioning the relief valve 102 close to the wet chamber 302 enables the relief valve 102 to be more sensitive to small additions of mass or fluid that enter the wet chamber 302 and contribute to a rise in pressure. Third, connecting the relief valve 102 directly to the wet chamber 302 reduces the fluid resistance encountered by leaked gas as it travels from the distal end to the relief valve 102. As a result, the relief valve 102 can quickly purge small amounts of fluid, thereby reducing the build-up of pressure. Fourth, positioning the electro-mechanical pressure switch 108 and the electrically-operated solenoid valve 110 within the ablation system 204 provides convenience for interfacing with the internal computer controlled system.

The fluid purging system 100 of the present invention can be integrated into other systems to serve similar purposes. The objectives of the fluid purging system 100 are as follows. First, to maintain fluid pressure within the wet chamber 302 below a pre-determined level by incorporating a relief valve 102 having a pre-set cracking pressure at a desirable level. Second, to capture and detect relieved fluid that exits the relief valve 102 using a pressure switch 108. Third, to purge pressurized fluid from the system and to relay the information to the computer controlled system. Ultimately, the fluid purging system 100 enables a fluid system to operate at a maximum set pressure, automatically detects abnormal pressure rise, electronically communicates to a central computer control system, and automatically purges the pressurized fluid and brings the pressure down to a safe level.

While the description above refers to particular embodiments of the present invention, it will be understood that many modifications may be made without departing from the spirit thereof.

What is claimed is:

1. A catheter system, comprising:
    a catheter assembly having a balloon adjacent its distal end, with a fluid chamber defined adjacent the balloon; and
    a fluid purging system, comprising:
        a spring-energized relief valve having an inlet port that is directly coupled to the fluid chamber to receive incoming fluid, and an outlet port through which incoming fluid is relieved, the relief valve having a pre-set cracking pressure, the outlet port fluidly coupled to a pressurized chamber;
        an electro-mechanical pressure switch which detects the presence of any fluid in the pressurized chamber; and
        an electrically operated solenoid valve which functions as a pressure exhaust valve that is opened when the pressure switch detects the presence of any fluid in the pressurized chamber;
    wherein the pressure switch and the solenoid valve are in fluid communication with the pressurized chamber;
    wherein when the internal fluid pressure at the fluid chamber rises above the pre-set cracking pressure, the overpressure fluid is purged by delivering it through the relief valve to the pressurized chamber to be purged by the solenoid valve.

2. The system of claim 1, wherein the catheter is a cryocatheter.

3. The system of claim 2, wherein the computer system purges all pressurized fluid within the pressurized chamber and the cryocatheter once the pressure switch is activated.

4. The system of claim 2, wherein the relief valve connects directly to the cryocatheter.

5. The system of claim 2, wherein the computer system shuts down all incoming fluid delivered to the pressurized chamber and to the cryocatheter once the pressure switch is activated.

6. The system of claim 1, wherein the pressure switch and the solenoid valve are positioned in an ablation system.

7. The system of claim 6, wherein the pressure switch and the solenoid valve are in communication with a computer controlled system.

8. The system of claim 1, wherein the pre-set cracking pressure is set within the range of 30 psig to 550 psig.

9. The system of claim 8, wherein the pressure switch electronically relays a message to a computer controlled system when it detects fluid in the pressurized chamber.

10. The system of claim 9, wherein the switching pressure of the pressure switch is designed to be less than the cracking pressure of the relief valve.

11. The system of claim 9, wherein the pressure switch detects pressure rise within the range of 0.10 psig to 25.0 psig.

12. The system of claim 1, wherein the outlet port of the relief valve is connected to a purging tube.

13. The system of claim 12, wherein a purging connector couples the purging tube and the pressurized chamber.

14. The system of claim 12, wherein the purging tube stores balloon liquid escaped from the relief valve during normal operation without activating the pressure switch.

15. The system of claim 1, wherein the relief valve is in series with the solenoid valve, and in series with the pressure switch.

\* \* \* \* \*